(12) United States Patent
Thorsen et al.

(10) Patent No.: US 12,004,547 B2
(45) Date of Patent: Jun. 11, 2024

(54) RECOVERY OF NITRATE REDUCTASE ACTIVITY

(71) Applicant: Chr. Hansen A/S, Hoersholm (DK)

(72) Inventors: Tina Malling Thorsen, Hoersholm (DK); George Nabin Baroi, Hoersholm (DK); Robin Taponen, Hoersholm (DK); Jakob Soeltoft-Jensen, Hoersholm (DK); Birgitte Yde, Hoersholm (DK)

(73) Assignee: Chr. Hansen A/S, Hoersholm (DK)

( * ) Notice: Subject to any disclaimer, the term of this patent is extended or adjusted under 35 U.S.C. 154(b) by 802 days.

(21) Appl. No.: 17/051,844

(22) PCT Filed: May 3, 2019

(86) PCT No.: PCT/EP2019/061422
§ 371 (c)(1),
(2) Date: Oct. 30, 2020

(87) PCT Pub. No.: WO2019/211458
PCT Pub. Date: Nov. 7, 2019

(65) Prior Publication Data
US 2021/0315239 A1  Oct. 14, 2021

(30) Foreign Application Priority Data

May 4, 2018 (EP) .................................. 18170807
Jul. 18, 2018 (EP) .................................. 18184186

(51) Int. Cl.
| | | |
|---|---|---|
| A23L 5/41 | (2016.01) | |
| A23L 13/40 | (2023.01) | |
| C12N 1/20 | (2006.01) | |
| C12N 9/06 | (2006.01) | |
| C12R 1/44 | (2006.01) | |

(52) U.S. Cl.
CPC .............. *A23L 5/41* (2016.08); *A23L 13/45* (2016.08); *C12N 1/20* (2013.01); *C12N 9/0044* (2013.01); *C12N 2500/34* (2013.01); *C12N 2500/35* (2013.01); *C12N 2500/38* (2013.01); *C12R 2001/44* (2021.05); *C12Y 107/99004* (2013.01)

(58) Field of Classification Search
CPC .. A23L 5/41; A23L 13/45; C12N 1/20; C12N 9/0044; C12N 2500/34; C12N 2500/35; C12N 2500/38; C12Y 107/99004; C12Y 107/990044
USPC ..................................................... 426/262
See application file for complete search history.

(56) References Cited

U.S. PATENT DOCUMENTS

| | | |
|---|---|---|
| 9,351,516 B2 | 5/2016 | Nissen et al. |
| 9,848,615 B2 | 12/2017 | Bisgaard-Frantzen et al. |
| 2011/0300591 A1 | 12/2011 | Gilet et al. |

FOREIGN PATENT DOCUMENTS

| | | | |
|---|---|---|---|
| CN | 1566322 A | 1/2005 | |
| CN | 1566323 A | 1/2005 | |
| CN | 101795572 A | 8/2010 | |
| CN | 104147605 A | 11/2014 | |
| CN | 104745501 A | 7/2015 | |
| EP | 0 259 739 A1 | 3/1988 | |
| EP | 1 441 027 A1 | 7/2004 | |
| EP | 1441027 A1 * | 7/2004 | ............. A23C 9/123 |
| RU | 2427624 C1 | 8/2011 | |
| WO | WO-2008/154536 A1 | 12/2008 | |
| WO | WO-2012/021783 A2 | 2/2012 | |
| WO | WO-2013/186348 A1 | 12/2013 | |
| WO | WO-2013186348 A1 * | 12/2013 | ............... A23B 4/22 |
| WO | WO-2015/140211 A1 | 9/2015 | |

OTHER PUBLICATIONS

Gotterup, J. et al. Meat Sci. 78: 492-501 (Year: 2008).*
"Colorimetry and Spectrophotometry" Vogel's Textbook of Quantitative Chemical Analysis, 5th Edition. Longman. p. 702. ISBN 0-582-44693-7 (1989).
Brooijmans et al., "Lactobacillus plantarum WCFS1 Electron Transport Chains", Applied and Environmental microbiology, vol. 75, No. 11, p. 3580-3585 (Jun. 2009).
Cárcoba et al. "Influence of cryoprotectants on the viability and acidifying activity of frozen and freeze-dried cells of the novel starter strain *Lactococcus lactis* subsp. *lactis* CECT 5180," Eur Food Res Technol., vol. 211, pp. 433-437, (2000).
Chavarri et al., "Cryoprotective Agents for Frozen Concentrated Starters from Non-Bitter *Streptococcus lactis* Strains", Biotechnology Letters, vol. 10, No. 1, pp. 11-16 (1988).
Conrad et al., "Stabilization and Preservation of Lactobacillus acidophilus in Saccharide Matrices", Cryobiology, vol. 41, pp. 17-24, 2000.
Dodds et al., "Incidence of Nitrite-Depleting Lactic Acid Bacteria in Cured Meats and in Meat Starter Cultures", Journal of Food Protection, vol. 47, No. 1, pp. 7-10 (Jan. 1984).

(Continued)

*Primary Examiner* — Hamid R Badr
(74) *Attorney, Agent, or Firm* — Foley & Lardner LLP

(57) ABSTRACT

The present invention is related to the field of reddening of food products. In particular the present invention relates to the preservation or optimization of nitrate reductase activity of frozen and/or dried lactic acid bacteria cultures or Micrococcaceae cultures (particularly cultures comprising one or more species of *Staphylococcus* having nitrate reductase activity).

18 Claims, No Drawings

(56) References Cited

OTHER PUBLICATIONS

Gøtterup et al., "Colour formation in fermented sausages by meat-associated staphylococci with different nitrite- and nitrate-reductase activities", Meat science, vol. 78, No. 4, pp. 492-501 (2008).
Hugenholtz, Jeroen, "Citrate metabolism in lactic acid bacteria", FEMS Microbiology Reviews 12, pp. 164-178, 1993.
Jakubowska et al., "Evaluation of Lactic Acid Streptococci for the Preparation of Frozen Concentrated Starter Cultures", Acta Microbiologica Polonica, vol. 29, No. 2, pp. 134-144 (1980).
Mogensen et al., "Inventory of Microorganisms with a Documented History of use in Food", Bulletin of the IDF No. 377, pp. 10-19 (2002).
Pinarkara, Yasemin, "Effect of Cryogenics on Survival During Drying and Storage of Freeze Dried Lactic Acid Bacteria", Intl. Scientific Researches Journal, vol. 72, No. 2, p. 82-94 (Feb. 2016).

\* cited by examiner

RECOVERY OF NITRATE REDUCTASE ACTIVITY

CROSS-REFERENCE TO RELATED APPLICATIONS

The present application is the U.S. National Stage of International Application No. PCT/EP2019/061422, filed May 3, 2019, and claims priority to European Patent Application Nos. 18170807.4 filed May 4, 2018, and 18184186.7 filed Jul. 18, 2018.

FIELD OF THE INVENTION

The present invention is related to the field of reddening of food products and microbial cultures. In particular, the present invention relates to the preservation of nitrate reductase activity of frozen and/or dried lactic acid bacteria cultures or Micrococcaceae cultures with the use of a specific survival enhancer and the use of said culture for reddening of meat products. Finally, the invention provides a method for increasing the nitrate reductase activity of a lactic acid bacteria and/or Micrococcaceae bacteria (such as e.g. a *Staphylococcus* strain) having nitrate reductase activity by use of citric acid or a salt thereof as cryoprotective agent.

BACKGROUND ART

Color formation and color stability are amongst the most critical quality traits of processed meat products and thus of great importance to the meat industry. The characteristic cured color can be derived from the concentration of heme pigments (myoglobin, hemoglobin), their chemical states and additives such as nitrogen oxides and reducing agents. In standard fermented meat products, such as salami, the characteristic cured color is a result of the chemical reaction between compounds derived from added nitrite/nitrate and the naturally occurring red myoglobin leading to the simultaneous formation of the bright red nitrosylmyoglobin, in which an axial ligand nitric oxide (NO) is coordinated to the central $Fe^{2+}$ in heme.

Despite of all its desired properties (color formation, microbiologic safety), the safety of nitrite to human health has been questioned. Nitrite can cause the formation of unwanted compounds in cured meat, like N-nitrosamines which are questionable in regard to health. These compounds can be formed in principle due to the reaction of nitrite with secondary amines and amino acids in muscle proteins as well as in the gastrointestinal tract.

The use of strains from lactic acid bacteria culture or Micrococcaceae culture for color formation is based on their ability to reduce inorganic nitrate to nitrite which is further degraded into the above described nitric oxide (NO), the active compound in the color formation process. Strains having high nitrate-reductase activity reported a significantly faster color formation in meat (Meat Science 2008 April: 78(4): 492-501), The nitrate could be provided directly as nitrate salt or indirectly with a natural nitrate source (vegetable powders). Even if a nitrite salt is added, the addition of strains from the specified groups is recommended as nitrite is partially re-converted to nitrate.

Commercial starter cultures are commonly distributed as frozen cultures. At the low temperature the frozen cultures, most metabolic activities in the cell cease and cells can be maintained in this suspended, but viable, state for extended periods.

Concentrated frozen cultures are commercially very interesting since the cultures can be inoculated directly into the production container. By using concentrated frozen cultures, the end-user avoids the otherwise obligatory, time-consuming intermediary fermentation step during which the starter culture is amplified, and the end-user reduces the risk of contamination significantly. Concentrated cultures may be referred to as DVS—direct vat Set™ cultures.

As an alternative to concentrated frozen cultures, concentrated freeze-dried DVS™ cultures may be prepared. These cultures have an additional advantage in that they can be shipped without refrigeration.

In general, possible damaging effects of freezing and thawing on the viability of living cells have been ascribed to cell dehydration and the formation of ice crystals in the cytosol during freezing.

An article by F. J. Chavarri et al. (Biotechnology letters, vol 10, 1, 11-16 (1988), "Cryoprotective agents for frozen concentrated starters from non-bitter *Streptococcus Lactis* strains") describes the storage viability of a frozen pure *Streptococcus lactis* culture may be improved by addition of 5% lactose or 5% sucrose. The lactose or sucrose worked as cryoprotective agents. *Streptococcus lactis* is a former name of *Lactococcus lactis* subsp. *lactis*.

Similarly, an article by R. Cárcoba et al (Eur Food Res Technol (2000) 211, 433-437, "Influence of cryoprotectants on the viability and acidifying activity of frozen and freeze-dried cells of the novel starter strain *Lactococcus lactis* subsp. *lactis* CECT 5180") describes that storage viability of a frozen pure *Lactococcus lactis* subsp. *lactis* culture could be improved by addition of different cryoprotective agents such as sugars (lactose, sucrose and trehalose), glutamic acid and gelatin.

The viability of freeze-dried cultures may also be improved by use of other cryoprotective agents. For instance, EP0259739 describes several different cryoprotective agents for freeze-dried cultures, including citric acid for stabilizing lactic acid bacteria. The patent does not disclose agents for stabilization of Micrococcaceae bacteria, or species of the family Staphylococcaceae (such as species of the *Staphylococcus* genus).

A number of other prior art documents also describe the use of citric acid or citrate as cryoprotective agents (see EP1441027, RU2427624, Pinarkara 2016, Conrad 2000, Jakubowska 1980). These do not disclose stabilization of Micrococcaceae bacteria, or species of the family Staphylococcaceae (such as species of the *Staphylococcus* genus).

Further, there are problems with loss of nitrate reductase activity during freezing and drying of bacteria such as Micrococcaceae bacteria or species of the family Staphylococcaceae (such as species of the *Staphylococcus* genus) even when using known cryoprotectants have been tested. So, there is a need for effective protectants that can be added to concentrated cultures used in the food industry, particularly the meat industry, for protection e.g. preserving or increasing the nitrate reductase activity of bacteria during freezing and drying. Improved stability of nitrate reductases during freezing and drying lead to improved color formation in food products.

SUMMARY OF THE INVENTION

The inventors of the present invention have surprisingly found that a bacterium having nitrate reductase activity, such as a lactic acid bacterium and Micrococcaceae bacteria cultures having nitrate reductase activity in the presence of citric acid or citrate have increased stability and/or preservation with regard to nitrate reductase activity during freezing and/or freeze-drying leading to an increased reddening when using the cultures for coloring of food products containing myoglobin. For example, the examples included herein below demonstrate that different formulations of *Streptococcus* species all including citrate improved and/or preserved the nitrate reductase activity of the frozen or freeze-dried culture over other formulations.

Therefore, in a first aspect the present invention relates to a concentrated culture comprising lactic acid bacteria and/or Micrococcaceae bacteria (e.g. a *Staphylococcus* specie) having nitrate reductase activity and comprising citric acid or a salt thereof (citrate).

The second aspect of the present invention relates to a method for making a frozen concentrated culture comprising:
  a) mixing a formulation comprising citric acid or a salt thereof (citrate) and lactic acid bacteria and/or Micrococcaceae bacteria (e.g. a *Staphylococcus* specie) having nitrate reductase activity;
  b) freezing the resulting mixture of a) to obtain a frozen material; and
  c) packing the frozen material.

The third aspect of the present invention relates to a method for making a dried concentrated culture comprising:
  a) mixing a formulation comprising a citrate and lactic acid bacteria and/or Micrococcaceae bacteria (e.g. a *Staphylococcus* specie) having nitrate reductase activity;
  b) drying the resulting mixture of a) to obtain a dried material;
  c) optionally grinding the obtained dried material of b); and
  d) packing the dried material.

The fourth aspect of the present invention relates to a method for making a freeze-dried concentrated culture comprising
  a) mixing a citrate and lactic acid bacteria and/or Micrococcaceae bacteria (e.g. a *Staphylococcus* specie) having nitrate reductase activity;
  b) freezing the resulting mixture of a) to obtain a frozen material;
  c) subliming water from the frozen material by freeze drying the material of b); and,
  d) packing the freeze-dried material of c).

The fifth aspect of the present invention relates to a method for reddening of a food product comprising the steps of
  a) adding the concentrated culture of the present invention to a food product; and
  b) fermenting, ripening or curing the food product with the concentrated culture of the present invention.

A sixth aspect of the present invention is directed to a food product comprising a composition according to the first aspect of the invention.

In a seventh aspect the present invention relates to the use of a composition according to the first aspect of the invention for reddening of a food product.

An eighth aspect of the invention relates to the use of citric acid or a salt thereof, for preserving and/or increasing the nitrate reductase activity of a bacteria selected from the group consisting of lactic acid bacteria and Micrococcaceae bacteria (such as a *Staphylococcus* specie).

A ninth aspect of the invention relates to a method for increasing the nitrate reductase activity of a bacteria having nitrate reductase activity selected from the group consisting of lactic acid bacteria and Micrococcaceae bacteria (such as e.g. a *Staphylococcus* strain) having nitrate reductase activity comprising the steps of:
  a) mixing a formulation comprising a citrate and lactic acid bacteria and/or Micrococcaceae bacteria (such as e.g. a *Staphylococcus* specie) having nitrate reductase activity to obtain a mixture comprising citrate and bacteria;
  b) optionally freezing the resulting mixture of a) to obtain a frozen material;
  c) drying the mixture of a), or the frozen material of step b), to obtain a dried material; and
  d) optionally packing the frozen material obtained from step b) or the dried material of step c) to obtain a packaged product.

DETAILED DESCRIPTION OF THE INVENTION

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising", "having", "including" and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

The present invention relates to a concentrated culture comprising a bacterium having nitrate reductase activity such as selected from the group consisting of lactic acid bacteria and Micrococcaceae bacteria (e.g. a *Staphylococcus* specie) and citric acid or citrate (i.e. a salt thereof).

The present invention relates to a concentrated culture of lactic acid bacteria and/or Micrococcaceae bacteria (e.g. a *Staphylococcus* specie) having nitrate reductase activity and a formulation comprising a citrate.

The term "lactic acid bacteria and/or Micrococcaceae bacteria having nitrate reductase activity" as used herein refers to species of lactic acid bacteria and/or Micrococcaceae bacteria which is capable of converting nitrate to nitrite.

As used herein the term "lactic acid bacterium" (LAB) designates a gram-positive, microaerophilic or anaerobic bacterium which ferments sugars with the production of acids including lactic acid (as the predominantly produced acid), acetic acid and propionic acid. The industrially most useful lactic acid bacteria are mostly found among species of the order Lactobacillales, for example *Lactococcus* species (spp.), *Streptococcus* spp., *Lactobacillus* spp. Such as *L. fermentum, L. pensosus* and *L. Plantarum, Leuconostoc* spp., *Pediococcus* spp. Such as *P. pentosaceus* and *P. acidilactici, Brevibacterium* spp, *Enterococcus* spp. and *Propionibacterium* spp. Additionally, lactic acid producing bacteria belonging to the group of the strict anaerobic bacteria, bifidobacteria, i.e. *Bifidobacterium* spp. which are frequently used as food starter cultures alone or in combination with lactic acid bacteria, are generally included in the group of lactic acid bacteria. In one embodiment of the invention, the lactic acid bacteria may be any lactic acid bacteria having nitrate reductase activity.

In one embodiment of the invention, the lactic acid bacteria may be a specie of the order Lactobacillales, such as a specie of the family Lactobacillaceae, such as a specie of the genus *Lactobacillus*. Thus, in one embodiment of the invention, the lactic acid bacteria is a specie of the genus *Lactobacillus* for examples a specie of *Lactobacillus pentosus*.

In a preferred embodiment of the present invention the *Lactobacillus pentosus* specie is the *Lactobacillus pentosus* strain CHCC4196 that was deposited with the Deutsche Sammlung von Mikroorganismen and Zellkulturen (DSMZ) under the accession no. DSM 25011.

Although part of another family and order than Lactobacillales, even certain bacteria of the genus *Staphylococcus* (e.g.: *S. carnosus*, *S. equorum*, *S. sciuri*, *S. vitulinus* and *S. xylosus*) have been referred to as LAB (Mogensen et al. (2002) Bulletin of the IDF No. 377, 10-19).

Staphylococci are Gram-positive organisms that grow singly, in pairs, in chains, or in clusters. They are members of the family Staphylococcaceae, which in turn is of the order Bacillales, and the class Bacilli. The *Staphylococcus* specie may be any *Staphylococcus* specie having nitrate reductase activity such as e.g. a *Staphylococcus* selected from the group consisting of *Staphylococcus vitulinus*, a *Staphylococcus carnosus* and a *Staphylococcus xylosus* specie. Other *Staphylococcus* species of interest are *S. simulans, S. saprophyticus, S. lentus, S. pasteuri, S. sciuri, S. haemolyticus, S. warneri, S. equorum, S. cohnii, S. epidermidis, S. hominis, S. capitis, S. intermedius* and *S. succinus*. Thus in one embodiment of the invention, the lactic acid bacteria having nitrate reductase activity is a specie selected from the group consisting of *Staphylococcus vitulinus, Staphylococcus carnosus, Staphylococcus xylosus, S. simulans, S. saprophyticus, S. lentus, S. pasteuri, S. sciuri, S. haemolyticus, S. warneri, S. equorum, S. cohnii, S. epidermidis, S. hominis, S. capitis, S. intermedius* and *S. succinu* and more preferably the lactic acid bacteria having nitrate reductase activity is a specie selected from the group consisting of *Staphylococcus vitulinus, Staphylococcus carnosus, Staphylococcus xylosus*.

In a preferred embodiment of the present invention the *Staphylococcus* specie having nitrate reductase activity is a *Staphylococcus vitulinus* specie or a *Staphylococcus carnosus* specie having nitrate reductase activity.

In a more preferred embodiment the *Staphylococcus* specie having nitrate reductase activity is a *Staphylococcus carnosus* specie.

In a preferred embodiment of the present invention the *Staphylococcus vitulinus* specie is selected from the group consisting of the *Staphylococcus vitulinus* strain CHCC10896 that was deposited with the Deutsche Sammlung von Mikroorganismen und Zellkulturen (DSMZ) under the accession no. DSM 25789, the *Staphylococcus vitulinus* strain CHCC11576 that was deposited with the Deutsche Sammlung von Mikroorganismen und Zellkulturen (DSMZ) under the accession no. DSM 27311 and mutants derived thereof. In another preferred embodiment of the present invention the *Staphylococcus carnosus* specie is a *Staphylococcus carnosus* strain CHCC4055 that was deposited with the Deutsche Sammlung von Mikroorganismen und Zellkulturen (DSMZ) under the accession no. DSM 32779 and mutants derived thereof.

Micrococcaceae is a family of bacteria containing gram-positive spherical cells that occur singly or in pairs, tetrads, packets, irregular masses, or even chains. Free-living, saprophytic, parasitic, and pathogenic species occur. The type genus is *Micrococcus*. The Micrococcaceae bacteria may be any Micrococcaceae bacteria having nitrate reductase activity. Particular Micrococcaceae bacteria of interest are species of the genus *Kocuria*.

Other genera belonging to the family of Micrococcaceae are *Actinomycetales. Acaricomes, Arthrobacter, Auritidibacter, Citricoccus, Enteractinococcus, Kocuria, Micrococcus, Nesterenkonia, Renibacterium, Rothia, Sinomonas, Yaniella* and *Zhihengliuella*. Thus, in one embodiment of the invention the bacteria having nitrate reductase activity is one or more species selected from the group consisting of *Actinomycetales. Acaricomes, Arthrobacter, Auritidibacter, Citricoccus, Enteractinococcus, Kocuria, Micrococcus, Nesterenkonia, Renibacterium, Rothia, Sinomonas, Yaniella* and *Zhihengliuella*. In a more preferred embodiment, the bacteria having nitrate reductase activity is one or more species selected from the group consisting of species of the genus *Kocuria*.

In a preferred embodiment of the present invention the *Kocuria* specie is a *Kocuria salsicia*. In a more preferred embodiment of the present invention the *Kocuria* specie is selected from the *Kocuria salsicia* strain CHCC5184 that was deposited with the Deutsche Sammlung von Mikroorganismen und Zellkulturen (DSMZ) under the accession no. DSM 32827, the *Kocuria salsicia* strain CHCC5185 that was deposited with the Deutsche Sammlung von Mikroorganismen und Zellkulturen (DSMZ) under the accession no. DSM 32828 and mutants derived thereof.

In a preferred embodiment of the present invention the concentrated culture comprises a *Kocuria* specie and/or a *Staphylococcus* specie having nitrate reductase activity and a formulation comprising a citrate. Thus, in a preferred embodiment, the concentrated culture comprises a bacterium having nitrate reductase activity selected from the group consisting of *Kocuria* species and *Staphylococcus* species and a formulation comprising citric acid or a salt thereof (citrate).

In the present context, the term "mutant" should be understood as a strain derived from a strain of the invention by means of e.g. genetic engineering, radiation and/or chemical treatment. It is preferred that the mutant is a functionally equivalent mutant, e.g. a mutant that has substantially the same, or improved, properties (e.g. regarding nitrate reductase activity) as the mother strain. Such a mutant is a part of the present invention. Especially, the term "mutant" refers to a strain obtained by subjecting a strain of the invention to any conventionally used mutagenization treatment including treatment with a chemical mutagen such as ethane methane sulphonate (EMS) or N-methyl-N'-nitro-N-nitroguanidine (NTG), UV light or to a spontaneously occurring mutant. A mutant may have been subjected to several mutagenization treatments (a single treatment should be understood one mutagenization step followed by a screening/selection step), but it is presently preferred that no more than 20, or no more than 10, or no more than 5, treatments (or screening/selection steps) are carried out.

In a presently preferred mutant less than 1%, less than 0.1, less than 0.01, less than 0.001% or even less than 0.0001% of the nucleotides in the bacterial genome have been replaced with another nucleotide, or deleted, compared to the mother strain.

In a preferred embodiment of the present invention the nitrate reductase activity of the specie is improved by at least 10%, such as at least 20%, such as at least 30%, such as at least 40%, such as at least 50% compared to a specie not being in the presence of a citrate after freezing or drying treatment.

The percentage improvement of the nitrate reductase activity of a *Staphylococcus* specie in question can be readily determined by the determination of conversion rate of nitrate to nitrite (nitrate reductase activity) and by measuring the concentration of nitrite to a given time e.g. in a kinetic set-up of the Griess test (Reference to: Colorimetry and Spectrophotometry" Vogel's Textbook of Quantitative Chemical Analysis, 5th Edition. Longman. p. 702. ISBN 0-582-44693-7) as described in the Examples herein.

The formulation comprising citric acid or a salt thereof (a citrate) may comprise only citric acid or a salt thereof (e.g. the formulation may be only citrate) or it may comprise other additional ingredients. Thus, the concentrated culture according to the invention may comprise or consist of one or more strains of a bacteria having nitrate reductase activity selected from the group consisting of lactic acid bacteria and Micrococcaceae, (e.g. one or more species of *Staphylococcus*), and citrate or a salt thereof.

The citric acid or citrate may be any citrate or salt thereof, such as magnesium citrate, trimagnesium citrate, monosodium citrate, disodium citrate, trisodium citrate and/or tripotassium citrate. Optionally, the citrate is a hydrated from. In a preferred embodiment of the present invention the citrate is a sodium citrate, particularly trisodium citrate, e.g. trisodium citrate monohydrate.

The amount of citric acid or citrate is at least 0.05% w/w based on the total composition before drying or freezing, such as at least 0.1%, 0.2%, 0.3%, 0.4%, 0.5% such as at least 0.6% based on the total composition before drying or freezing. The amount of citrate is at most 10% w/w, such as at most 8%, 6%, 5%, 4%, 3% such as at most 2% based on the total composition before drying or freezing.

The amount of citric acid or citrate is at least 0.2% w/w based on the total composition after drying or freezing, such as at least 0.5%, 1%, 2%, 3%, 4%, 5%, 6%, 7%, 8% based on the total composition after drying or freezing.

The amount of citric acid or citrate is at most 50% w/w, such as at most 40%, 30%, 25%, 20%, 16%, 15%, 14%, 13% such as at most 12% based on the total composition after drying or freezing.

In a specific embodiment, the concentrated culture according to the invention is dried (e.g. freeze dried) and comprises from about 0.1% w/w to about 30% w/w citric acid or a salt thereof (e.g. trisodium citrate), such as for example from about 0.5% w/w to about 25% w/w citric acid or a salt thereof (e.g. trisodium citrate), such as for example from about 1.0% w/w to about 20.0% w/w citric acid or a salt thereof (e.g. trisodium citrate), more preferably from about 1.0% w/w to about 10.0% w/w citric acid or a salt thereof (e.g. trisodium citrate), and even more preferably from about 2.0% w/w to about 8.0% w/w citric acid or a salt thereof.

Sucrose is a disaccharide and may be further comprised in the formulations comprising citric acid according to the invention. Thus, in one embodiment, wherein the concentrated culture is dried (e.g. freeze-dried), the dried culture comprises from about 0.5% w/w to about 30.0% w/w sucrose, e.g. from about 1.0% w/w to about 8.0% w/w sucrose, or e.g. from about 2.0% w/w to about 5.0% w/w sucrose.

Maltodextrin is a polysaccharide and may be further comprised in the formulations comprising citric acid according to the invention. Maltodextrins are classified by DE (dextrose equivalent) and have a DE between 3 and 20. The higher the DE value, the shorter the glucose chains, the higher the sweetness, the higher the solubility, and the lower heat resistance. In a preferred embodiment the concentrated culture of the present invention further comprises maltodextrin which may be of a DE from 3 to 20, whereof maltodextrin DE 12 is preferred. Thus, in a preferred embodiment of the invention, the concentrated culture comprises or consists of a formulation citric acid or a salt thereof and lactic acid bacteria and/or Micrococcaceae bacteria (e.g. one or more species of *Staphylococcus*) and a polysaccharide (e.g. maltodextrin).

In one embodiment, wherein the concentrated culture is dried (e.g. freeze-dried), the dried culture comprises from about 0.5% w/w to about 30.0% w/w maltodextrin, e.g. from about 1.0% w/w to about 15.0% w/w maltodextrin, or e.g. from about 2.0% w/w to about 12.0% w/w maltodextrin.

Sugar alcohols such as inositol may be further comprised in the formulations comprising citric acid according to the invention. In one embodiment of the invention, the concentrated culture of the present invention further comprises inositol or a derivative thereof (e.g. a form of inositol phosphate).

Thus, in one embodiment the concentrated culture of the present invention comprises or consists of a lactic acid bacterium and/or Micrococcaceae bacteria (e.g. a *Staphylococcus* specie) having nitrate reductase activity, citric acid or a salt thereof, and inositol or a derivative thereof (e.g. a form of inositol phosphate).

In another specific embodiment, the concentrated culture of the present invention comprises or consists of a *Staphylococcus* specie having nitrate reductase activity, citric acid or a salt thereof, and inositol.

Accordingly, in one embodiment, wherein the concentrated culture is dried (e.g. freeze-dried), the dried culture comprises from about 0.5% w/w to about 20.0% w/w sugar alcohol (e.g. inositol or a derivate thereof), such as from about 0.5% w/w to about 30.0% w/w inositol, e.g. from about 1.0% w/w to about 15.0% w/w inositol, or e.g. from about 2.0% w/w to about 12.0% w/w inositol.

In a particular embodiment of the present invention the citrate is either citric acid or salts of citric acid.

The concentrated culture of the present invention may further comprise a monosaccharide, a disaccharide, a trisaccharide, an oligosaccharide and/or a polysaccharide.

The disaccharide may be selected from but are not limited to the group consisting of sucrose, lactose and maltose.

In a more specific embodiment of the invention, the concentrated culture comprises or consists of one or more species of lactic acid bacteria and/or Micrococcaceae, (e.g. one or more species of *Staphylococcus*), citrate or a salt thereof, and a disaccharide, preferably sucrose.

In one embodiment of the invention, the concentrated culture comprises one or more polysaccharides. The polysaccharide may be selected but are not limited to the group consisting of maltodextrin.

In a more specific embodiment of the invention, the concentrated culture comprises or consists of one or more species of lactic acid bacteria and/or Micrococcaceae, (e.g. one or more species of *Staphylococcus*), citrate or a salt thereof, and a polysaccharide, preferably maltodextrin, and optionally water.

Thus, in a more specific embodiment of the invention, the concentrated culture comprises or consists of one or more species of lactic acid bacteria and/or Micrococcaceae, (e.g. one or more species of *Staphylococcus*), citrate or a salt thereof, a disaccharide, e.g. sucrose, a polysaccharide (e.g. maltodextrin), and optionally water.

Thus, in an even more specific embodiment of the invention, the concentrated culture consists of one or more species of a lactic acid bacteria and/or Micrococcaceae, (e.g. one or more species of *Staphylococcus*), citrate or a salt thereof, a disaccharide (e.g. sucrose), a polysaccharide (e.g. maltodextrin), and optionally water.

In yet an even more specific embodiment of the invention, the concentrated culture comprises or consists of one or more species of a lactic acid bacteria and/or Micrococcaceae, (e.g. one or more species of *Staphylococcus*), citrate or a salt thereof, sucrose, maltodextrin, and optionally water.

In yet an even more specific embodiment of the invention, the concentrated culture comprises or consists of one or more species of *Staphylococcus*, citrate or a salt thereof, sucrose, maltodextrin, and optionally water.

The concentrated culture of the present invention may further comprise an amino acid, a peptide and/or a protein.

The method for obtaining the concentrated culture of the present composition is by mixing a formulation of citrate and one or more species lactic acid bacteria and/or Micrococcaceae bacteria having nitrate reductase activity. The obtained composition may be dried or frozen afterwards.

In aspects wherein the mixture comprising citric acid or a salt thereof and bacteria is frozen, the freezing may be performed by allowing contacting the mixture with a cryogenic object, fluid or gas, e.g. by contacting the mixture with liquid nitrogen, such as e.g. by allowing the mixture to drip into liquid nitrogen, thereby forming pellets, threads or strings, wherein pellets are preferred. Alternatively, the mixture may be frozen (for example in a freezer) in a tray en bloc, and may thereafter be divided into smaller entities, (e.g. pellets) for example ground into smaller particles.

In a preferred embodiment of the invention, the mixture comprising citric acid or a salt thereof and bacteria is frozen in a tray and thereafter freeze-dried.

In a preferred embodiment of the invention, the mixture comprising citric acid or a salt thereof and bacteria is frozen in a tray, freeze-dried and ground into particles.

In another preferred embodiment of the invention, the mixture comprising citric acid or a salt thereof and bacteria is frozen in a tray, thereafter freeze-dried and ground.

In aspects wherein the mixture comprising citric acid or a salt thereof, and a bacteria is dried to obtain a dried material, said drying may be performed using various techniques of the art, e.g. vacuum drying, spray drying, lyophilization, fluidized bed drying and/or desiccation. In a preferred embodiment, drying is performed by freeze drying or spray drying, and in a particular embodiment by freeze drying. Thus, the method of drying may be but are not limited to vacuum drying, freeze drying and/or spray drying.

In a preferred embodiment a dried culture is obtained by
  a) mixing a formulation of citrate and a lactic acid bacterium and/or Micrococcaceae bacteria having nitrate reductase activity and optionally other ingredients;
  b) drying the resulting mixture of a) to obtain a dried material;
  c) optionally grinding the obtained dried material of b); and
  d) packing the dried material.

The drying may be performed by but are not limited to vacuum-drying, freeze-drying and/or spray-drying.

In a more preferred embodiment of the present invention the freeze-dried culture is obtained by
  a) mixing a formulation of citrate and a lactic acid bacterium and/or Micrococcaceae bacteria having nitrate reductase activity and optionally other ingredients;
  b) freezing the resulting mixture of a) to obtain a frozen material;
  c) subliming water from the frozen material to freeze-dry the material of b);
  d) Optionally grinding the obtained freeze-dried material of c); and
  e) packing the freeze-dried material.

In another preferred embodiment of the present invention a spray-dried culture is obtained by
  a) mixing a formulation of citrate and a lactic acid bacterium and/or Micrococcaceae bacteria having nitrate reductase activity and optionally other ingredients;
  b) spray drying the resulting mixture of a) to obtain a spray-dried material;
  c) packing the spray dried material.

In another preferred embodiment of the present invention a frozen culture is obtained by
  a) mixing a formulation of citrate and lactic acid bacteria and/or Micrococcaceae bacteria having nitrate reductase activity and optionally other ingredients;
  b) freezing the resulting mixture of a) to obtain a frozen material;
  c) packing the frozen material.

In a particular embodiment of the present invention the concentrated culture is pelletized.

In a preferred embodiment of the present invention the method for obtaining the concentrated culture of the present composition is by mixing a formulation of citrate and a *Staphylococcus* having nitrate reductase activity. The obtained culture may be dried or frozen afterwards.

The method of drying may be but are not limited to vacuum-drying, freeze-drying and/or spray-drying.

In a preferred embodiment a dried culture is obtained by
  a) mixing a formulation of citrate and a *Staphylococcus* specie having nitrate reductase activity and optionally other ingredients;
  b) drying the resulting mixture of a) to obtain a dried material;
  c) optionally grinding the obtained dried material of b); and
  d) packing the dried material.

The drying may be performed by but are not limited to vacuum-drying, freeze-drying and/or spray drying.

In a more preferred embodiment of the present invention the freeze-dried culture is obtained by
  a) mixing a formulation of citrate and a *Staphylococcus* specie having nitrate reductase activity and optionally other ingredients;
  b) freezing the resulting mixture of a) to obtain a frozen material;
  c) subliming water from the frozen material to freeze-dry the material of b);
  d) Optionally grinding the obtained freeze-dried material of c); and
  e) packing the freeze-dried material.

In another preferred embodiment of the present invention a spray-dried culture is obtained by
  a) mixing a formulation of citrate and a *Staphylococcus* specie having nitrate reductase activity and optionally other ingredients;
  b) spray-drying the resulting mixture of a) to obtain a spray-dried material;

c) packing the spray dried material.

In another preferred embodiment of the present invention a frozen culture is obtained by
a) mixing a formulation of citrate and a *Staphylococcus* specie having nitrate reductase activity and optionally other ingredients;
b) freezing the resulting mixture of a) to obtain a frozen material;
c) packing the frozen material.

In a particular embodiment of the present invention the concentrated culture is pelletized.

One aspect of the invention relates to a method for increasing the nitrate reductase activity of a bacteria having nitrate reductase activity selected from the group consisting of lactic acid bacteria and Micrococcaceae bacteria (such as e.g. a *Staphylococcus* species). Thus, one embodiment of said method involves the steps of:
a) mixing a formulation comprising citric acid or a salt thereof, and a bacterium having nitrate reductase activity selected from the group consisting of lactic acid bacteria and Micrococcaceae bacteria (such as e.g. a *Staphylococcus* species) to obtain a mixture comprising citrate and bacteria;
b) optionally freezing the resulting mixture of a) to obtain a frozen material;
c) drying the mixture of a) or the frozen material of step b) to obtain a dried material; and
d) optionally packing the frozen material obtained from step b) or the dried material of step c) to obtain a packaged product.

In a preferred embodiment, said method for increasing the nitrate reductase activity of a bacteria having nitrate reductase activity involves the steps of:
a) mixing a formulation comprising a citrate and a bacterium having nitrate reductase activity selected from the group consisting of lactic acid bacteria and Micrococcaceae bacteria (such as e.g. a *Staphylococcus* species) to obtain a mixture comprising citrate and bacteria;
b) freezing the resulting mixture of a) to obtain a frozen material;
c) drying the frozen material of step b) to obtain a dried material; and
d) optionally packing the dried material of step c) to obtain a packaged product.

One aspect of the invention relates to the use of a formulation comprising citric acid or a salt thereof for preserving and/or increasing the nitrate reductase activity of a bacteria selected from the group consisting of lactic acid bacteria and Micrococcaceae bacteria (such as a *Staphylococcus* specie). In this aspect, formulation comprising citric acid or salt thereof may be defined by any of the embodiments described herein. Further, the bacteria selected from the group consisting of lactic acid bacteria and Micrococcaceae bacteria (such as a *Staphylococcus* specie) may selected according to any embodiment described herein.

The present invention furthermore relates to a method for reddening of a food product comprising the steps of adding the concentrated culture of the present invention to a food product, and fermenting, ripening or curing the food product with the concentrated culture.

The food product may be any product based on a food source containing myoglobin. In a preferred embodiment the food product is a meat product.

The meat product may be any product with a content of meat. The meat may be bovine meat, pork meat, poultry meat, game meat or any other category of meat.

The food product may also be a product based on fish and/or based on crustaceans.

In a preferred embodiment the concentrated culture comprising lactic acid bacteria and/or Micrococcaceae bacteria is added in a quantity of from $1.0 \times 10^8$ to $1.0 \times 10^{12}$ CFU/kg, such as from $1.0 \times 10^9$ to $1.0 \times 10^{11}$ CFU/kg lactic acid bacteria and/or Micrococcaceae bacteria. Preferably the composition is added in a quantity of from $2.0 \times 10^9$ to $5.0 \times 10^{10}$ CFU/kg of lactic acid bacteria and/or Micrococcaceae bacteria.

In a preferred embodiment the concentrated culture comprising *Staphylococcus* specie is added in a quantity of from $1.0 \times 10^8$ to $1.0 \times 10^{12}$ CFU/kg, such as from $1.0 \times 10^9$ to $1.0 \times 10^{11}$ CFU/kg *Staphylococcus* specie. Preferably the composition is added in a quantity of from $2.0 \times 10^9$ to $5.0 \times 10^{10}$ CFU/kg of *Staphylococcus* specie.

The invention is also directed to a food product obtainable by the method for reddening a food product described above or a food product obtainable by the use for reddening a food product.

Items

The following numbered items further describe the invention:
1. A concentrated culture comprising a formulation of citrate and lactic acid bacteria and/or Micrococcaceae bacteria having nitrate reductase activity.
2. The concentrated culture of item 1, wherein the Micrococcaceae bacteria is a *staphylococcus* specie having nitrate reductase activity.
3. The concentrated culture of item 2, wherein the *staphylococcus* specie is selected from the group consisting of *Staphylococcus* xylosus, carnosus and/or vitulinus.
4. The concentrated culture of any preceding items, wherein the citrate is either citric acid or salts of citric acid.
5. The concentrated culture of any preceding items further comprising a monosaccharide, a disaccharide, a trisaccharide and/or an oligosaccharide and/or a polysaccharide.
6. The concentrated culture of item 5, wherein the disaccharide may be selected from the group consisting of sucrose, lactose, maltose and trehalose.
7. The composition of item 5, wherein the polysaccharide is maltodextrin.
8. The composition of any preceding items further comprising an amino acid, a peptide and/or a protein.
9. The composition of any of the preceding items, wherein the composition is dry.
10. The composition of any of the preceding items, wherein the composition is a frozen, freeze dried, vacuum dried and/or spray dried composition.
11. A method for making the concentrated culture of item 1 comprising:
   a) mixing lactic acid bacteria and/or Micrococcaceae bacteria having nitrate reductase activity with a formulation comprising a citrate.
12. A method for making a dried concentrated culture comprising:
   a) mixing a formulation comprising a citrate and lactic acid bacteria and/or Micrococcaceae bacteria having nitrate reductase activity;
   b) drying the resulting mixture of a) to obtain a dried material;
   c) optionally grinding the obtained dried material of b); and
   d) packing the dried material.

13. The method of item 12, wherein the drying is performed by vacuum drying, freeze drying and/or spray drying.
14. A method for making a frozen concentrated culture comprising:
   a) mixing a formulation comprising a citrate and lactic acid bacteria and/or Micrococcaceae bacteria having nitrate reductase activity;
   b) freezing the resulting mixture of a) to obtain a frozen material; and
   c) packing the frozen material.
15. A method for making a freeze-dried concentrated culture comprising:
   a) mixing formulation comprising a citrate and lactic acid bacteria and/or Micrococcaceae bacteria having nitrate reductase activity;
   b) freezing the resulting mixture of a) to obtain a frozen material;
   c) subliming water from the frozen material to freeze-dry the material of b);
   d) optionally grinding the obtained freeze-dried material of c); and
   e) packing the freeze-dried material.
16. A method for making a spray dried concentrated culture comprising:
   a) mixing a formulation comprising a citrate and lactic acid bacteria and/or Micrococcaceae bacteria having nitrate reductase activity;
   b) spray drying the resulting mixture of a) to obtain a spray dried material; and
   c) packing the spray dried material.
17. A method for making the concentrated culture of item 2 comprising:
   a) mixing a Staphylococcus specie having nitrate reductase activity with a formulation comprising a citrate.
18. The method of any of items 11 to 16, wherein the Micrococcaceae bacteria is a Staphylococcus specie.
19. A method for making a dried concentrated culture comprising:
   a) mixing a Staphylococcus specie having nitrate reductase activity with a formulation comprising a citrate;
   b) drying the resulting mixture of a) to obtain a dried material;
   c) optionally grinding the obtained dried material of b); and
   d) packing the dried material.
20. A method for making a frozen concentrated culture comprising:
   a) mixing a formulation comprising a citrate and a Staphylococcus specie having nitrate reductase activity;
   b) freezing the resulting mixture of a) to obtain a frozen material;
   c) packing the frozen material.
21. A method for making a freeze-dried concentrated culture comprising:
   a) mixing a formulation comprising a citrate and a Staphylococcus specie having nitrate reductase activity;
   b) freezing the resulting mixture of a) to obtain a frozen material;
   c) subliming water from the frozen material to freeze-dry the material of b);
   d) optionally grinding the obtained freeze-dried material of c); and
   e) packing the freeze-dried material.
22. A method for making a spray dried concentrated culture comprising:
   a) mixing a formulation comprising a citrate and a Staphylococcus specie having nitrate reductase activity;
   b) spray drying the resulting mixture of a) to obtain a spray dried material; and
   c) packing the spray dried material.
23. The method according to items 17 to 22, wherein the Staphylococcus specie having nitrate reductase activity is a Staphylococcus vitulinus specie or a Staphylococcus carnosus specie.
24. The method according to item 23, wherein the Staphylococcus vitulinus specie is selected from the group consisting of the Staphylococcus vitulinus specie CHCC10896 that was deposited with the Deutsche Sammlung von Mikroorganismen und Zellkulturen (DSMZ) under the accession no. DSM 25789, the Staphylococcus vitulinus specie CHCC11576 that was deposited with the Deutsche Sammlung von Mikroorganismen und Zellkulturen (DSMZ) under the accession no. DSM 27311 and mutants derived thereof.
25. The method according to any of items 11 to 24, wherein the concentrated culture is pelletized.
26. A method for reddening a food product comprising the steps of
   a) adding the composition according to any of items 1 to 10 to a meat product; and
   b) fermenting, ripening or curing the meat product with the composition.
27. The method according to item 26, wherein the food product is a meat product.
28. Use of the composition according to any of items 1 to 10 for reddening a food product.

Embodiments of the present invention are described below, by way of non-limiting examples.

EXAMPLES

The following method can be used for determining nitrate reductase activity (NRA): The nitrite reductase activity may be determined by using the Griess test for quantification of nitrite. The method is performed as a kinetic experiment, thereby monitoring the formation of nitrite (nitrate conversion) as a function of time. Reaction rates are obtained at different cell densities.

The results are reported as nitrite formed per time unit per active cell. Number of active cells per gram dry sample is measured by flow cytometry and staining with the membrane potential sensitive dye $DiOC_2(3)$ in accordance with "ISO 19344:2015 Milk and milk products—Starter cultures, probiotics and fermented products—Quantification of lactic acid bacteria by flow cytometry", protocol C.

To determine nitrate reductase activity, freeze dried bacteria are suspended in sodium phosphate buffer (pH 7) in four different concentrations for each sample targeting 0.6, 1.3, 1.9 and $2.5 \times 10^9$ active cells/mL. Magnetic stirring bars are added to the suspensions, and a layer of mineral oil is placed on top of to protect the samples from environmental oxygen. After temperature equilibration to 45° C., glucose and nitrate in sodium phosphate buffer (pH 7) are added to the samples. After 10, 20, 30, 40, 50 and 60 minutes a small aliquot of the suspension is aspired and transferred to phosphoric acid (1 M) for nitrite concentration determination.

Griess-Ilosvay reagent (sulfanilic acid and 1-naphthylamine in acetic acid) are added to the samples diluted in phosphoric acid. After brief incubation in the dark (5-30 minutes), spectrophotometric measurement of the diazotization product of nitrite and the Griess reagents are measured (absorbance 540 nm). By using a nitrite standard curve, the absorbance measured can be used to calculate the nitrite concentration in the samples investigated. The rate of nitrate conversion can then be determined for the different dilutions (cell concentrations) of a sample investigated and then in turn the rate of nitrate conversion per cell can be determined. The function of nitrite concentration formed pr. time versus cell concentration has to give a coefficient of determination above 0.975 ($R^2 > 0.975$, coefficient of correlation, $R > 0.95$) to be acceptable.

Example 1

Preparation for *Staphylococcus carnosus*

Formulation 1:

Tri sodium citrate: 9.7%

Sucrose: 5.6%

Maltodextrine DE12: 12.9%

Water: 71.8%

Formulation 2:

Sodium ascorbate: 27.8%

Inositol: 15.6%

Water: 56.6%

The formulations were boiled at 100° C. for 20 minutes. The dose of the formulations was 100 g of concentrate of *Staphylococcus carnosus* mixed with 8 g of formulation 1 and 100 g of concentrate of *Staphylococcus carnosus* mixed with 12.4 g of formulation 2 and 100 g of concentrate of *Staphylococcus carnosus* used as negative control (not added any protectants). After mixing, samples were kept at −50° C. before freeze drying and grinding.

Nitrate reductase activity (NRA) before and after freeze drying were measured.

The determination of the conversion rate of nitrate to nitrite (nitrate reductase activity) of a *Staphylococcus* specie in question was determined by measurement of the concentration of nitrite to a given time e.g. in a kinetic set-up of the Griess test (Reference to: Colorimetry and Spectrophotometry" Vogel's Textbook of Quantitative Chemical Analysis, 5th Edition. Longman. p. 702. ISBN 0-582-44693-7) as described in the Examples herein. The results are listed in Table 1.

TABLE 1

Effects of different formulations on nitrate conversion rate (NRA) of *Staphylococcus carnosus*

| Protectant | NRA of the cell concentrate before freeze drying | % NRA recovery after the freeze drying and grinding |
|---|---|---|
| Citrate | 65 | 62 |
| Sodium ascorbate | 65 | 9 |
| Negative control | 68 | 35 |

It was concluded that the NRA of the sample comprising citrate had a higher recovery by almost 2 times compared to a sample with no protectant added and a higher recovery by 7 times compared to the sample with sodium ascorbate.

Example 2

Preparation for *Staphylococcus vitulinus*

Formulation 1:

Tri sodium citrate: 9.7%

Sucrose: 5.6%

Maltodextrine DE12: 12.9%

Water: 71.8%

Formulation 2:

Sodium ascorbate: 27.8%

Inositol: 15.6%

Water: 56.6%

The formulations 1 and 2 were boiled at 100° C. for 20 minutes.

The dose of the formulations was 100 g of concentrate of *Staphylococcus vitulinus* mixed with 8 g of formulation 1 and 100 g of concentrate of *Staphylococcus vitulinus* mixed with 12.4 g of formulation 2 and 100 g of concentrate of *Staphylococcus carnosus* used as negative control (not added any protectant). After mixing, samples were kept at −50° C. before freeze drying and grinding. Nitrate conversion rate or NRA before and after freeze drying were measured. The determination of the conversion rate of nitrate to nitrite (nitrate reductase activity) of a *Staphylococcus* specie in question was determined by measurement of the concentration of nitrite to a given time e.g. in a kinetic set-up of the Griess test (Reference to: Colorimetry and Spectrophotometry" Vogel's Textbook of Quantitative Chemical Analysis, 5th Edition. Longman. p. 702. ISBN 0-582-44693-7) as described in the Examples herein. The results are listed in Table 2.

TABLE 2

Effects of different protectants on NRA of *Staphylococcus vitulinus*

| Additive | NRA of the cell concentrate before freeze-drying | % of NRA recovery after the freeze-drying and grinding |
|---|---|---|
| With Citrate | 44 | 98 |
| Sodium ascorbate | 21 | 12 |
| None | 43 | 53 |

It was concluded that the NRA recovery of the sample comprising citrate was almost 2 times higher compared to a sample with no protectant added and eight times higher compared to the sample with ascorbic acid.

Example 3

Effects of Different Formulations Comprising Inositol and Citrate on Nitrate Conversion Rate (NRA) of *Staphylococcus carnosus*

Different formulations comprising inositol were prepared according to Table 3 below. In the formulations, trisodium citrate monohydrate or sodium ascorbate was used in combination with inositol.

The formulations were boiled, mixed with concentrate of *Staphylococcus carnosus*, frozen and freeze dried as described in Example 1. The nitrate reductase activity was measured as described above.

TABLE 3

Different formulations of inositol and citrate

| # | Formul. name | Comments | Cryo dose kg/100 kg concentrate | NaAsc kg/100 kg | Citrate kg/100 kg | Inositol kg/100 kg | Water kg/100 kg |
|---|---|---|---|---|---|---|---|
| 3 | AI | Ascorbate control | 8 | 27.8 | 0 | 15.6 | 56.6 |
| 4 | CI | Citrate | 8 | 0 | 27.8 | 15.6 | 56.6 |
| 5 | CI | 0.5 × citrate | 8 | 0 | 13.9 | 15.6 | 70.5 |
| 6 | CI | 1 × citrate Repl. of formulation #4 | 8 | 0 | 27.8 | 15.6 | 56.6 |
| 7 | CI | 2 × citrate | 8 | 0 | 55.6 | 15.6 | 28.8 |
| 8 | CI | 2 × cryo dose | 16 | 0 | 27.8 | 15.6 | 56.6 |

This resulted in freeze dried products as shown in Table 4 below.

TABLE 4

Comparison of NRA of inositol formulations

| # | Formul. name | FD CF | FD g | g NaAsc/ kg FD | g Citrate/ kg FD | g Inositol/ kg FD | NRA PFD | NRA FD | % Recovery NRA |
|---|---|---|---|---|---|---|---|---|---|
| 3 | AI | 3.9 | 256 | 80 | 0 | 45 | 49 | 5 | 11% |
| 4 | CI | 4.0 | 250 | 0 | 82 | 46 | 42 | 23 | 54% |
| 5 | CI | 4.3 | 233 | 0 | 44 | 50 | 107 | 41 | 38% |
| 6 | CI | 4.3 | 233 | 0 | 89 | 50 | 66 | 42 | 64% |
| 7 | CI | 4.4 | 227 | 0 | 181 | 51 | 55 | 42 | 77% |
| 8 | CI | 4.2 | 238 | 0 | 161 | 90 | 74 | 38 | 51% |

As can be seen from the table above comparing the use of the AI formulation comprising ascorbic acid and inositol to the CI formulations comprising citric acid and inositol, the presence of citrate in the formulation resulted in a higher recovery of nitrate reductase activity in the freeze-dried product as measured by the nitrate conversion rate (NRA) of *Staphylococcus carnosus*.

Example 4

Effects of Different Initial Formulations Comprising Sucrose, Maltodextrin on Nitrate Conversion Rate (NRA) of *Staphylococcus carnosus*

Different formulations comprising sucrose and maltodextrin were prepared according to Table 5 below. The formulations comprised sodium ascorbate or trisodium citrate monohydrate in addition to 5.5 kg sucrose/100 kg bacterial concentrate and 13 kg Maltodextrin DE12/100 kg bacterial concentrate. The formulations were boiled, mixed with concentrate of *Staphylococcus carnosus*, frozen and freeze dried as described in Example 1. The nitrate reductase activity was measured as described above.

TABLE 5

Different initial formulations comprising sucrose and maltodextrin

| # | Formul. name | Comments | Cryo dose kg/100 kg conc. | NaAsc kg/100 kg | Citrate kg/100 kg | Sucrose kg/100 kg | Malto DE12 kg/100 kg | Water kg/100 kg |
|---|---|---|---|---|---|---|---|---|
| 7 | ASM | Ascorbate control | 12.4 | 9.5 | 0 | 5.5 | 13 | 72 |
| 8 | ASM | Ascorbate control | 20 | 9.5 | 0 | 5.5 | 13 | 72 |
| 9 | CSM | Citrate | 12.4 | 0 | 9.5 | 5.5 | 13 | 72 |

This resulted in freeze dried products as shown in Table 6 below.

TABLE 6

Comparison of NRA of initial sucrose and maltodextrin formulations

| # | Formul. name | FD CF | FD g | g NaAsc/ kg FD | g Citrate/ kg FD | g sucrose/ kg FD | g malto DE12/ kg FD | NRA PFD | NRA FD | % Recovery NRA |
|---|---|---|---|---|---|---|---|---|---|---|
| 7 | ASM | 4.1 | 244 | 43 | 0 | 25 | 59 | 42 | 7 | 17% |
| 8 | ASM | 4 | 250 | 63 | 0 | 37 | 87 | 35 | 5 | 13% |
| 9 | CSM | 4.1 | 244 | 0 | 43 | 25 | 59 | 42 | 25 | 60% |

As can be seen from Table 6 above, in the formulations comprising sucrose and maltodextrin, the presence of citrate in the formulation resulted in higher NRA in the frozen and freeze-dried product compared to the formulations comprising sodium ascorbate.

Example 5

Effects of Different Further Formulations Comprising Sucrose, Maltodextrin on Nitrate Conversion Rate (NRA) of *Staphylococcus carnosus*

In addition to the initial formulations shown in Example 4 above, further formulations comprising various concentrations of ascorbate or citrate and invariant concentrations of sucrose and maltodextrin were prepared according to Table 7 below. The formulations comprised sodium ascorbate or trisodium citrate monohydrate in addition to 5.5 kg sucrose/100 kg bacterial concentrate and 13 kg Maltodextrin DE12/100 kg bacterial concentrate. The formulations were boiled, mixed with concentrate of *Staphylococcus carnosus*, frozen and freeze dried as described in Example 1. The nitrate reductase activity was measured as described above.

TABLE 7

Different further formulations comprising sucrose and maltodextrin

| # | Formul. name | Comments | Cryo dose kg/100 kg conc. | NaAsc kg/100 kg | Citrate kg/100 kg | Sucrose kg/100 kg | Malto DE12 kg/100 kg | Water kg/100 kg |
|---|---|---|---|---|---|---|---|---|
| 10 | ASM | Ascorbate | 12.4 | 9.5 | 0 | 5.5 | 13 | 72 |
| 11 | ASM | Ascorbate | 20 | 9.5 | 0 | 5.5 | 13 | 72 |
| 12 | CSM | 0.5 × citrate | 12.4 | 0 | 4.75 | 5.5 | 13 | 76.75 |
| 13 | CSM | 1 × citrate Repl. of # 9 | 12.4 | 0 | 9.5 | 5.5 | 13 | 72 |
| 14 | CSM | 2 × citrate | 12.4 | 0 | 19.0 | 5.5 | 13 | 62.5 |
| 15 | CSM | 2 × cryo dose | 25 | 0 | 9.5 | 5.5 | 13 | 72 |

This resulted in freeze dried products as shown in Table 8 below.

TABLE 8

Comparison of NRA of further sucrose and maltodextrin formulations

| # | Formul. name | FD CF | FD g | g NaAsc/ kg FD | g citrate/ kg FD | g sucrose/ kg FD | g malto DE12/ kg FD | NRA PFD | NRA FD | % Recovery NRA |
|---|---|---|---|---|---|---|---|---|---|---|
| 10 | ASM | 4.3 | 233 | 45 | 0 | 26 | 62 | 78 | NA | <30% |
| 11 | ASM | 4.3 | 233 | 68 | 0 | 39 | 93 | 87 | NA | <30% |
| 12 | CSM | 4.4 | 227 | 0 | 23 | 27 | 63 | 94 | 43 | 46% |
| 13 | CSM | 4.4 | 227 | 0 | 46 | 27 | 63 | 92 | 41 | 45% |
| 14 | CSM | 4.1 | 244 | 0 | 86 | 25 | 59 | 59 | 41 | 69% |
| 15 | CSM | 4.2 | 238 | 0 | 80 | 46 | 109 | 80 | 29 | 36% |

As can be seen in the results of Table 8 above, that in the additional formulations comprising invariant concentrations of sucrose and maltodextrin, but different concentrations of ascorbate and citrate, the presence of citrate in the formulation resulted in higher NRA in the freeze dried product compared to the formulations comprising sodium ascorbate, which had a NRA recovery below 30%.

Example 6

Statistical Experimental Set-Up to Test the Effects of Different Concentrations of Sucrose, Maltodextrin and Citrate on Nitrate Reductase Activity (NRA) of *Staphylococcus carnosus*

In addition to the formulations shown in Examples 4 and 5 above, as statistical experimental set-up was used to test the effects on NRA in formulations with variant concentrations of ascorbate or citrate, sucrose and maltodextrin DE 12 prepared according to Table 9 below. A triplicate test was performed to establish a centre point average NRA and std. dev (see formulation numbers 20-22 below).

The formulations were boiled, mixed with concentrate of *Staphylococcus carnosus*, frozen and freeze dried as described in Example 1. The nitrate reductase activity was measured as described above.

TABLE 9

Statistical set-up formulations comprising citrate, sucrose and maltodextrin

| # | Formul. name | Comments | Cryo dose kg/100 kg conc. | Citrate kg/100 kg | Sucrose kg/100 kg | Malto DE12 kg/100 kg | Water kg/100 kg |
|---|---|---|---|---|---|---|---|
| 16 | CSM | DOE setup | 12.4 | 2.42 | 2.82 | 6.45 | 88.3 |
| 17 | CSM | DOE setup | 12.4 | 2.42 | 8.47 | 6.45 | 82.7 |
| 18 | CSM | DOE setup | 12.4 | 2.42 | 2.82 | 19.35 | 75.4 |
| 19 | CSM | DOE setup | 12.4 | 2.42 | 8.47 | 19.35 | 69.8 |
| 20 | CSM | DOE setup | 12.4 | 8.47 | 5.65 | 12.90 | 73.0 |
| 21 | CSM | DOE setup | 12.4 | 8.47 | 5.65 | 12.90 | 73.0 |
| 22 | CSM | DOE setup | 12.4 | 8.47 | 5.65 | 12.90 | 73.0 |
| 23 | CSM | DOE setup | 12.4 | 14.52 | 2.82 | 6.45 | 76.2 |
| 24 | CSM | DOE setup | 12.4 | 14.52 | 8.47 | 6.45 | 70.6 |
| 25 | CSM | DOE setup | 12.4 | 14.52 | 2.82 | 19.35 | 63.3 |
| 26 | CSM | DOE setup | 12.4 | 14.52 | 8.47 | 19.35 | 57.7 |

This resulted in freeze dried products as shown in Table 10 below.

TABLE 10

Comparison of NRA of further sucrose and maltodextrin formulations

| # | Formul. name | FD CF | FD g | g citrate/ kg FD | g sucrose/ kg FD | g malto DE12/ kg FD | NRA PFD | NRA FD | % Recovery NRA |
|---|---|---|---|---|---|---|---|---|---|
| 16 | CSM | 5.1 | 198 | 13 | 16 | 36 | 87 | 51 | 59% |
| 17 | CSM | 5.0 | 199 | 13 | 47 | 36 | 73 | 48 | 65% |
| 18 | CSM | 4.8 | 207 | 13 | 15 | 103 | 72 | 51 | 72% |
| 19 | CSM | 4.7 | 214 | 12 | 44 | 100 | 74 | 45 | 61% |
| 20 | CSM | 4.7 | 211 | 44 | 30 | 67 | 72 | 52 | 71% |
| 21 | CSM | 4.8 | 210 | 44 | 30 | 68 | 75 | 56 | 74% |
| 22 | CSM | 4.8 | 210 | 45 | 30 | 68 | 69 | 48 | 70% |
| 23 | CSM | 4.8 | 208 | 77 | 15 | 34 | 75 | 55 | 73% |
| 24 | CSM | 4.7 | 214 | 75 | 44 | 33 | 78 | 49 | 63% |
| 25 | CSM | 4.5 | 221 | 72 | 14 | 96 | 75 | 48 | 64% |
| 26 | CSM | 4.4 | 227 | 70 | 41 | 94 | 74 | 52 | 70% |

The center point average NRA and std. dev was determined using the NRA of formulation numbers 20-22. This resulted in an average NRD in the frozen formulation of 72% and a std. deviation of 4.5%. For the corresponding freeze dried formulations, the average NRD was 52% and a std. deviation of 7.5%. The average recovery of NRA in the freeze dried formulations was determined to be 72% with a std. deviation of 3.1%.

As can be seen from the data in Table 10 above, NRA was preserved to a relatively high extent in all the different formulations in the experimental set-up independently of the concentrations of maltodextrin and sucrose.

Example 7

Effects of Different Formulations Comprising Sucrose, Maltodextrin on Nitrate Conversion Rate (NRA) of *Staphylococcus vitulinus*

To confirm the effects demonstrated in Examples 3 and 4 on a different species of *Staphylococcus*, a similar experiment was performed using a strain of *Staphylococcus vitulinus*.

Formulations comprising various concentrations of ascorbate or citrate and invariant concentrations of sucrose and maltodextrin were prepared according to Table 11 below. The formulations comprised sodium ascorbate or trisodium citrate monohydrate in addition to 5.5 kg sucrose/100 kg bacterial concentrate and 13 kg Maltodextrin DE12/100 kg bacterial concentrate. The formulations were boiled, mixed with concentrate of *Staphylococcus carnosus*, frozen and freeze dried as described in Example 1. The nitrate reductase activity was measured as described above.

TABLE 11

Different formulations comprising sucrose and maltodextrin

| # | Formul. name | Note | Cryo dose kg/100 kg conc. | NaAsc kg/100 kg | Citrate kg/100 kg | Inositol kg/100 kg | Sucrose kg/100 kg | Malto DE12 kg/100 kg | Water kg/100 kg |
|---|---|---|---|---|---|---|---|---|---|
| 31 | ASM | Ascorbate - control | 9.5 | 9.5 | 0 | 0 | 5.5 | 13 | 72 |
| 32 | CSM | 0.5 × citrate | 12.4 | 9.5 | 4.75 | 0 | 5.5 | 13 | 76.75 |
| 33 | CSM | 1 × citrate | 12.4 | 0 | 9.50 | 0 | 5.5 | 13 | 72 |
| 34 | CSM | 2 × citrate | 12.4 | 0 | 19.00 | 0 | 5.5 | 13 | 62.5 |
| 35 | CI | 0.5 × citrate | 8 | 0 | 9.93 | 15.6 | 0 | 0 | 74.47 |
| 36 | CI | 1.6 × citrate | 8 | 0 | 15.4 | 4.33 | 0 | 0 | 80.2 |
| 37 | CI | 2 × citrate | 8 | 0 | 19.86 | 11.14 | 0 | 0 | 69 |
| 38 | CI | 2 × cryo dose | 16 | 0 | 15.4 | 8.67 | 0 | 0 | 75.9 |

This resulted in freeze dried products as shown in Table 12 below.

TABLE 12

Comparison of NRA of different formulations comprising *S. vitulinus*

| # | Formul. name | FD CF | FD g | g NaAsc/ kg FD | g citrate/ kg FD | g Inositol/ kg FD | g sucrose/ kg FD | g malto DE12/ kg FD | NRA FD | % Recovery NRA compared to ascorbate control |
|---|---|---|---|---|---|---|---|---|---|---|
| 31 | ASM | 4.6 | 717 | 48 | 0 | 0 | 28 | 66 | 1 | — |
| 32 | CSM | 4.8 | 208 | 0 | 25 | 0 | 29 | 69 | 6 | 86% |
| 33 | CSM | 4.7 | 213 | 0 | 49 | 0 | 29 | 67 | 8 | 89% |
| 34 | CSM | 4.4 | 227 | 0 | 92 | 0 | 27 | 63 | 11 | 92% |
| 35 | CI | 4.7 | 213 | 0 | 35 | 54 | 0 | 0 | 6 | 85% |
| 36 | CI | 4.3 | 233 | 0 | 49 | 14 | 0 | 0 | 31 | 97% |
| 37 | CI | 4.6 | 217 | 0 | 68 | 38 | 0 | 0 | 6 | 86% |
| 38 | CI | 3.1 | 323 | 0 | 66 | 37 | 0 | 0 | 34 | 98% |

As can be seen in the results of Table 12 above, for the formulations comprising invariant concentrations of sucrose and maltodextrin, and different concentrations of citrate, the presence of citrate in the formulation resulted in higher NRA in all the freeze dried products compared to the formulation comprising sodium ascorbate, which had a low NRA of 1.

Further, all the formulations comprising inositol and citrate had higher NRA than the formulation comprising ascorbate. Thus, the results of the example above confirm that citrate is useful for preserving and/or increasing the NRA of *Staphylococcus vitulinus*.

REFERENCES

EP0259739
EP1441027
RU2427624
R. Cárcoba et al (Eur Food Res Technol (2000) 211, 433-437, "Influence of cryoprotectants on the viability and acidifying activity of frozen and freeze-dried cells of the novel starter strain *Lactococcus lactis* subsp. *lactis* CECT 5180.
Colorimetry and Spectrophotometry" Vogel's Textbook of Quantitative Chemical Analysis, 5th Edition. Longman. p. 702. ISBN 0-582-44693-7
Conrad et al., "Stabilization and preservation of *Lactobacillus acidophilus* in saccharide matrices", Cryobiology, 41, p. 17-24, 2000.
Chavarri et al., "Cryoprotective agents for frozen concentrated starters from non-bitter *Streptococcus Lactis* strains", (Biotechnology letters, vol 10, 1, 11-16 (1988).
Gøtterup et al., "Colour formation in fermented sausages by meat-associated staphylococci with different nitrite- and nitrate-reductase activities", Meat science 2008 April; 78(4): 492-501.
Jukubowska et al., "Evaluation of lactic acid streptococci for the preparation of frozen concentrated starter cultures", Acta Microbiologica Polonica, vol. 29, no. 2, p. 134-144, 1980.
Mogensen et al., "Inventory of microorganisms with a documented history of use in food", (2002) Bulletin of the IDF No. 377, 10-19.
Pinarkara, Yasemin, "Effect of cryogenics on survival during drying and storage of freeze dried lactic acid bacteria", Intl. Scientific Researches Journal, Ponte, vol. 72, no. 2, p. 82-94, 2016

Deposits and Expert Solution

The applicant requests that a sample of the deposited micro-organisms stated below may only be made available to an expert, until the date on which the patent is granted.

The strain *Staphylococcus vitulinus* CHCC10896 that was deposited at Deutsche Sammlung von Mikroorganismen und Zellkulturen (DSMZ) GmbH, Inhoffenstr. 7B, D-38124 Braunschweig, Germany, on 15 Mar. 2012, under the accession No. DSM 25789.

The strain *Staphylococcus vitulinus* strain CHCC11576 has been deposited at Deutsche Sammlung von Mikroorganismen und Zellkulturen (DSMZ) GmbH, Inhoffenstr. 7B, D-38124 Braunschweig, Germany, on 11 Jun. 2013, under the accession No. DSM 27311.

The strain *Staphylococcus carnosus* strain CHCC4055 has been deposited at Deutsche Sammlung von Mikroorganismen und Zellkulturen (DSMZ) GmbH, Inhoffenstr. 7B, D-38124 Braunschweig, Germany, on 20 Mar. 2018, under the accession No. DSM 32779.

The strain *Lactobacillus pentosus* strain CHCC4196 has been deposited at Deutsche Sammlung von Mikroorganismen und Zellkulturen (DSMZ) GmbH Inhoffenstr. 7B, D-38124 Braunschweig, Germany, on 12 Jul. 2011 under the accession DSM 25011.

The strain *Kocuria salsicia* strain CHCC5184 has been deposited at Deutsche Sammlung von Mikroorganismen und Zellkulturen (DSMZ) GmbH Inhoffenstr. 7B, D-38124 Braunschweig, Germany, on 5 Jun. 2018 under the accession no. DSM 32827.

The strain *Kocuria salsicia* strain CHCC5185 has been deposited at Deutsche Sammlung von Mikroorganismen und Zellkulturen (DSMZ) GmbH Inhoffenstr. 7B, D-38124 Braunschweig, Germany, on 5 Jun. 2018 under the accession no. DSM 32828.

The deposits were made according to the Budapest treaty on the international recognition of the deposit of microorganisms for the purposes of patent procedure.

The invention claimed is:

1. A method for preserving or increasing nitrate reductase activity of lactic acid bacteria or Micrococcaceae bacteria having nitrate reductase activity, comprising preparing a mixture comprising citric acid or a salt thereof and bacteria having nitrate reductase activity to obtain a mixture, wherein the bacteria having nitrate reductase activity are selected from lactic acid bacteria and Micrococcaceae bacteria, and wherein the bacteria in the mixture are protected from loss of nitrate reductase activity due to one or more of freezing, drying, and freeze-drying, as compared to bacteria formulated without the citric acid or salt thereof.

2. The method according to claim 1, wherein the bacteria having nitrate reductase activity comprise Micrococcaceae bacteria of genus *Kocuria*.

3. The method according to claim 1, wherein the bacteria having nitrate reductase activity comprise one or more selected from *Staphylococcus carnosus* strain CHCC4055 deposited at Deutsche Sammlung von Mikroorganismen und Zellkulturen (DSMZ) under accession No. DSM 32779, *Staphylococcus vitulinus* strain CHCC10896 deposited with the Deutsche Sammlung von Mikroorganismen und Zellkulturen (DSMZ) under accession no. DSM 25789, and the *Staphylococcus vitulinus* specie strain CHCC11576 deposited with the Deutsche Sammlung von Mikroorganismen und Zellkulturen (DSMZ) under accession no. DSM 27311, and mutants derived therefrom.

4. The method according to claim 1, wherein the citric acid or salt thereof comprises trisodium citrate.

5. The method according to claim 1, wherein the mixture further comprises one or more selected from monosaccharides, disaccharides, trisaccharides, oligosaccharides, and polysaccharides.

6. The method according to claim 1, wherein the mixture further comprises a disaccharide selected from sucrose, lactose, maltose, and trehalose.

7. The method according to claim 1, further comprising freezing the mixture to obtain a frozen material.

8. The method according to claim 1, further comprising drying the mixture to obtain a dried material.

9. The method according to claim 8, wherein the drying is effected by one or more of desiccation, fluidized bed drying, freeze-drying, vacuum-drying, and spray-drying.

10. The method according to claim 1, further comprising freezing the mixture in a tray and thereafter freeze-drying the mixture.

11. The method according to claim 1, further comprising one or more of freezing, drying, and freeze-drying the mixture, and subsequently grinding or milling the mixture into smaller particles.

12. The method according to claim 1, wherein the bacteria having nitrate reductase activity comprise Staphylococcaceae bacteria.

13. The method according to claim 1, wherein the bacteria having nitrate reductase activity comprise bacteria of one or more *Staphylococcus* species selected from *Staphylococcus xylosus, Staphylococcus carnosus*, and *Staphylococcus vitulinus*.

14. The method according to claim 1, further comprising packing the material to obtain a packaged product.

15. The method according to claim 1, further comprising pelletizing the material.

16. A method for making a concentrated culture of bacteria having nitrate reductase activity, comprising mixing bacteria having nitrate reductase activity selected from the group consisting of lactic acid bacteria and Micrococcaceae bacteria having nitrate reductase activity with citric acid or a salt thereof to obtain the concentrated culture, wherein the bacteria in the concentrated culture are protected from loss of nitrate reductase activity due to one or more of freezing, drying, and freeze-drying, as compared to bacteria formulated without the citric acid or salt thereof.

17. A method for reddening a food product, comprising adding to a food product a concentrated culture comprising citric acid or a salt thereof and bacteria having nitrate reductase activity, wherein the bacteria having nitrate reductase activity are selected from the group consisting of lactic acid bacteria and Micrococcaceae bacteria having nitrate reductase activity, and wherein the bacteria in the concentrated culture are protected from loss of nitrate reductase activity due to one or more of freezing, drying, and freeze-drying, as compared to bacteria formulated without the citric acid or salt thereof; and fermenting, ripening or curing the food product with the concentrated culture.

18. The method according to claim 17, wherein the food product is a meat product.

* * * * *